(12) United States Patent
Salo

(10) Patent No.: US 6,892,095 B2
(45) Date of Patent: May 10, 2005

(54) METHOD AND APPARATUS FOR MONITORING LEFT VENTRICULAR WORK OR POWER

(75) Inventor: Rodney Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 493 days.

(21) Appl. No.: 10/036,639

(22) Filed: Dec. 31, 2001

(65) Prior Publication Data
US 2003/0125774 A1 Jul. 3, 2003

(51) Int. Cl.$^7$ ................................................ A61N 1/365
(52) U.S. Cl. ..................... 607/21; 607/24; 607/122; 600/505; 600/526
(58) Field of Search ............... 607/7, 17–21, 607/119, 122, 22, 24; 600/373, 374, 526, 505

(56) References Cited

U.S. PATENT DOCUMENTS

| | | |
|---|---|---|
| 3,995,623 A | 12/1976 | Blake et al. |
| 4,485,813 A * | 12/1984 | Anderson et al. ........... 600/488 |
| 4,674,518 A | 6/1987 | Salo |
| 4,686,987 A | 8/1987 | Salo et al. |
| 4,803,987 A | 2/1989 | Calfee et al. |
| 5,005,574 A | 4/1991 | Fearnot et al. |
| 5,036,849 A | 8/1991 | Hauck et al. |
| 5,174,299 A | 12/1992 | Nelson |
| 5,174,303 A | 12/1992 | Schroeppel |
| 5,190,035 A | 3/1993 | Salo et al. |
| 5,336,244 A | 8/1994 | Weijand |
| 5,464,434 A | 11/1995 | Alt |
| 5,831,159 A | 11/1998 | Renger |
| 5,876,399 A * | 3/1999 | Chia et al. .................... 606/41 |
| 6,096,061 A | 8/2000 | Alt et al. |
| 6,278,894 B1 | 8/2001 | Salo et al. |
| 6,309,350 B1 | 10/2001 | VanTassel et al. |
| 6,398,738 B1 * | 6/2002 | Millar ........................ 600/486 |
| 2001/0010009 A1 | 7/2001 | Bakels et al. |

* cited by examiner

Primary Examiner—Angela D. Sykes
Assistant Examiner—Roderick Bradford
(74) Attorney, Agent, or Firm—Crawford Maunu PLLC

(57) ABSTRACT

A body implantable system employs a lead system having at least one electrode and at least one thermal sensor at a distal end. The lead system is implanted within a patient's heart in a coronary vein of the left ventricle. The thermal sensor can be attached to a catheter that is disposed within an open lumen of the lead system. The thermal sensor senses a coronary vein temperature. The coronary vein temperature can be measured at a detector/energy delivery system and used as an activity indicator to adaptively control pacing rate. The measured coronary vein temperature can be also used with a left ventricular flow measurement to determine hemodynamic efficiency of the heart. A detected change in hemodynamic efficiency can be used by the detector/energy delivery system to modify the delivery of electrical pulses to the lead system.

17 Claims, 4 Drawing Sheets

METHOD AND APPARATUS FOR MONITORING LEFT VENTRICULAR WORK OR POWER

FIELD OF THE INVENTION

The invention relates to a method and apparatus for measuring left ventricular work, and more particularly to measuring work as a function of left ventricular blood temperature from a pacing/defibrillation lead implanted in a branch vein of the coronary sinus. The left ventricular blood temperature may be used with a left ventricular flow measurement to determine useful work and/or hemodynamic efficiency of the heart.

BACKGROUND OF THE INVENTION

Heart disease (cardiomyopathy) can cause a patient to exhibit symptoms of congestive heart failure (CHF). CHF is a result of the weakening of the heart's cardiac function, and is characterized by reduced pumping capacity and efficiency. Chronic cardiac rhythm problems can also be the result of cardiomyopathy. The modification of the heart's structure that causes the reduction in pumping capacity also causes modification of the heart's electrical characteristics. The heart's electrical pathways can become stretched out of shape and chemically damaged. This makes arrhythmias much more likely to occur in CHF patients.

Implantation of a pacemaker is a preferred method of treatment for arrhythmias in CHF patients. Although many types of heart problems may require a pacer, one method of treatment suited for CHF patients is known as cardiac resynchronization therapy (CRT). CRT uses a pacemaker with multiple pacing leads to coordinate the heart's four chambers to act together in a sequence that will pump blood more efficiently.

It is likely that CRT candidates will have various forms of cardiomyopathy, and these patients may exhibit other measurable symptoms of reduced cardiac function besides arrhythmia. The reduced cardiac function of the heart is taken into account when applying CRT in order to tailor the therapy based on the needs of a particular patient. Various external factors must also be taken into account by the pacing system, one of those factors being the current state of activity of the patient.

Rate adaptive pacemakers are currently used that can estimate body activity by detecting body activity or breathing rate and depth, and therefore modify the pacing rate applied to the heart. These indicators can give a rough estimate of metabolic demand for a given patient. It would be beneficial to have more accurate measures of metabolic demand, especially measures that can determine the pumping capacity and pumping efficiency of a heart in order to measure and improve the efficacy of therapy for the CHF patient.

For the reasons stated above, and for other reasons stated below which will become apparent to those skilled in the art upon reading the present specification, there is a need in the art for improved ventricular monitoring and therapy control. There exists a further need for a pacing system that provides a means of measuring cardiac workload and efficiency in order to offer more effective treatment for CHF patients. The present invention fulfills these and other needs, and provides several advantages over prior systems and techniques.

SUMMARY OF THE INVENTION

The present invention is directed to a method and apparatus for measuring left ventricular power and/or work. In one embodiment, a body implantable system includes a lead system having an elongated body, an open lumen, and at least one electrode at a distal end of the lead system. A sensing catheter is movably disposed within the open lumen of the lead system. A distal tip of the sensing catheter extends beyond a distal tip of the lead system. The sensing catheter includes at least one thermal sensor at a distal end of the sensing catheter. A detector/energy delivery system is coupled to the lead system. The detector/energy delivery system senses ventricular rhythms from the electrode(s) and senses blood temperature from the thermal sensor(s). The detector/energy delivery system also delivers an electrical signal to the electrode(s).

The thermal sensor may include a thermistor, thermocouple, fiber optic temperature probe, and/or a micro-electrical-mechanical systems (MEMS) temperature sensor. In one configuration, the detector/energy delivery system modifies the delivery of electrical signals based on the sensed blood temperature.

The body implantable system may further include a flow sensor that senses a cardiac output, with the detector/energy delivery system sensing a left ventricular flow rate from the flow sensor. The flow sensor may include a ventricular impedance sensor. The detector/energy delivery system can determine a hemodynamic efficiency of the heart using the sensed left ventricular flow rate and the sensed blood temperature. The detector/energy delivery system can be configured to modify the delivery of electrical signals based on the sensed left ventricular flow rate and the sensed blood temperature.

In another configuration, a body implantable system according to the present invention may include a ventricular thermal sensor for sensing a blood temperature entering the left ventricle. The ventricular thermal sensor is coupled to the detector/energy delivery system. The detector/energy delivery system further senses a temperature difference between the ventricular thermal sensor and the thermal sensor(s) at a distal end of the sensing catheter. The detector/energy delivery system can determine a hemodynamic efficiency of the heart using the sensed temperature difference. The detector/energy delivery system can also modify the delivery of electrical signals based on the sensed temperature difference.

The body implantable system may further include an activity sensor coupled to the detector/energy delivery system. The activity sensor can include an accelerometer and/or a minute ventilation sensor. The detector/energy delivery system can be configured to update a long term average blood temperature measurement from the thermal sensor(s), the long term average blood temperature updated at a state of rest as sensed by the activity sensor.

In another embodiment of the invention, a method of pacing a patient's heart involves providing a lead system into a coronary vein of the left ventricle of the patient's heart. The lead system includes an elongated body, at least one electrode at a distal end of the lead system, and at least one thermal sensor at a distal end of the lead system. The method further involves providing a flow sensor in the patient's heart, the flow sensor for sensing left ventricular flow. Ventricular electrical rhythms are measured at the electrode(s) to deliver synchronized electrical signals to the electrode(s). A coronary vein blood temperature is measured from the thermal sensor(s) and a left ventricular flow rate is measured from the flow sensor to adaptively modify the delivery of synchronized electrical signals.

The thermal sensor(s) can include a thermistor, thermocouple, fiber optic temperature probe, and/or a microelectrical-mechanical systems (MEMS) temperature sensor. The flow sensor can include a ventricular impedance sensor.

In one aspect of the method, adaptively modifying the delivery of synchronized electrical signals further involves determining hemodynamic efficiency using the coronary vein blood temperature and the left ventricular flow rate.

The method can involve measuring a coronary vein blood temperature from the thermal sensor(s) to update a long-term average coronary vein temperature. The method can further involve providing an activity sensor implantable within the patient, and updating a long-term average coronary vein temperature can further involve updating a long-term average coronary vein temperature at a state of rest as sensed by the activity sensor. In another aspect of the method, adaptively modifying the delivery of synchronized electrical signals can further include comparing a measured coronary vein blood temperature with a long-term average coronary vein temperature.

The method can further involve providing a ventricular thermal sensor for sensing a blood temperature entering the left ventricle. Adaptively modifying delivery of synchronized electrical signals delivered to the patient's heart can involve sensing a temperature difference between the ventricular thermal sensor and thermal sensor(s) at a distal end of the lead system.

In another embodiment of the invention, a method of pacing a patient's heart involves providing a lead system into a vein of the patient's heart. The lead system includes an elongated body, an open lumen, and at least one electrode at a distal end of the lead system. The method further involves introducing a sensing catheter within the open lumen of the lead system until a distal tip of the sensing catheter extends beyond a distal tip of the lead system. The sensing catheter comprises at least one thermal sensor at a distal end of the sensing catheter. Ventricular electrical rhythms are measured from the electrode(s) to deliver synchronized electrical signals to the electrode(s). A coronary vein blood temperature is measured from the thermal sensor(s) to adaptively modify delivery of the synchronized electrical signals. The thermal sensor(s) can include a thermistor, thermocouple, fiber optic temperature probe, and/or a microelectrical-mechanical systems (MEMS) temperature sensor.

One aspect of the method further involves providing a flow sensor in the patient's heart, the flow sensor sensing left ventricular flow. The flow sensor may include a ventricular impedance sensor. Adaptively modifying the delivery of the synchronized electrical signals may further involve measuring a left ventricular flow rate from the flow sensor. Adaptively modifying the delivery of synchronized electrical signals may also involve determining a hemodynamic efficiency from the coronary vein blood temperature and the left ventricular flow rate.

The method can involve measuring a coronary vein blood temperature from the thermal sensor(s) to update a long-term average coronary vein temperature. The method can further involve providing an activity sensor implantable within the patient, and updating a long-term average coronary vein temperature can further involve updating a long-term average coronary vein temperature at a state of rest as sensed by the activity sensor. The activity sensor can include an accelerometer and/or a minute ventilation sensor. In another aspect of the method, adaptively modifying the delivery of synchronized electrical signals can further include comparing a measured coronary vein blood temperature with a long-term average coronary vein temperature.

The method can further involve providing a ventricular thermal sensor for sensing a blood temperature entering the left ventricle. Adaptively modifying delivery of synchronized electrical signals delivered to the patient's heart can involve sensing a temperature difference between the ventricular thermal sensor and the thermal sensor(s) at a distal end of the lead system.

In another embodiment of the present invention, a body implantable system includes a lead system having an elongated body suitable for positioning into a coronary vein. At least one electrode is situated at a distal end of the elongated body. A thermal sensor is located proximal to the distal end of the elongated body, the thermal sensor sensing an average coronary sinus blood temperature at a location distal to the coronary sinus ostium when the electrode(s) is/are positioned in a coronary vein. A programmable circuit is coupled to the lead system. The programmable circuit determines a hemodynamic state from the sensed average coronary sinus blood temperature.

The thermal sensor may include a thermistor, thermocouple, fiber optic temperature probe, and/or a microelectrical-mechanical systems (MEMS) temperature sensor. In one configuration, an energy delivery system is coupled to the programmable circuit. The energy delivery modifies the delivery of electrical signals based on the sensed blood temperature.

The body implantable system may further include a flow sensor that senses a cardiac output, with the programmable circuit sensing a left ventricular flow rate from the flow sensor. The flow sensor may include a ventricular impedance sensor. The programmable circuit can determine a hemodynamic efficiency of the heart using the sensed left ventricular flow rate and the sensed blood temperature. The programmable circuit can be coupled to an energy delivery system. The energy delivery system is configured to modify the delivery of electrical signals based on the sensed left ventricular flow rate and the sensed blood temperature.

In another configuration, a body implantable system according to the present invention may include a ventricular thermal sensor for sensing a blood temperature entering the left ventricle. The ventricular thermal sensor is coupled to the programmable circuit. The programmable circuit further senses a temperature difference between the ventricular thermal sensor and the thermal sensor(s) at a distal end of the sensing catheter. The programmable circuit can determine a hemodynamic efficiency of the heart using the sensed temperature difference. The programmable circuit can be coupled to an energy delivery system. The energy delivery system modifies the delivery of electrical signals based on the sensed temperature difference.

The body implantable system may further include an activity sensor coupled to the programmable circuit. The activity sensor can include an accelerometer and/or a minute ventilation sensor. The programmable circuit can be configured to update a long term average blood temperature measurement from the thermal sensor(s). The long term average blood temperature is updated at a state of rest as sensed by the activity sensor.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
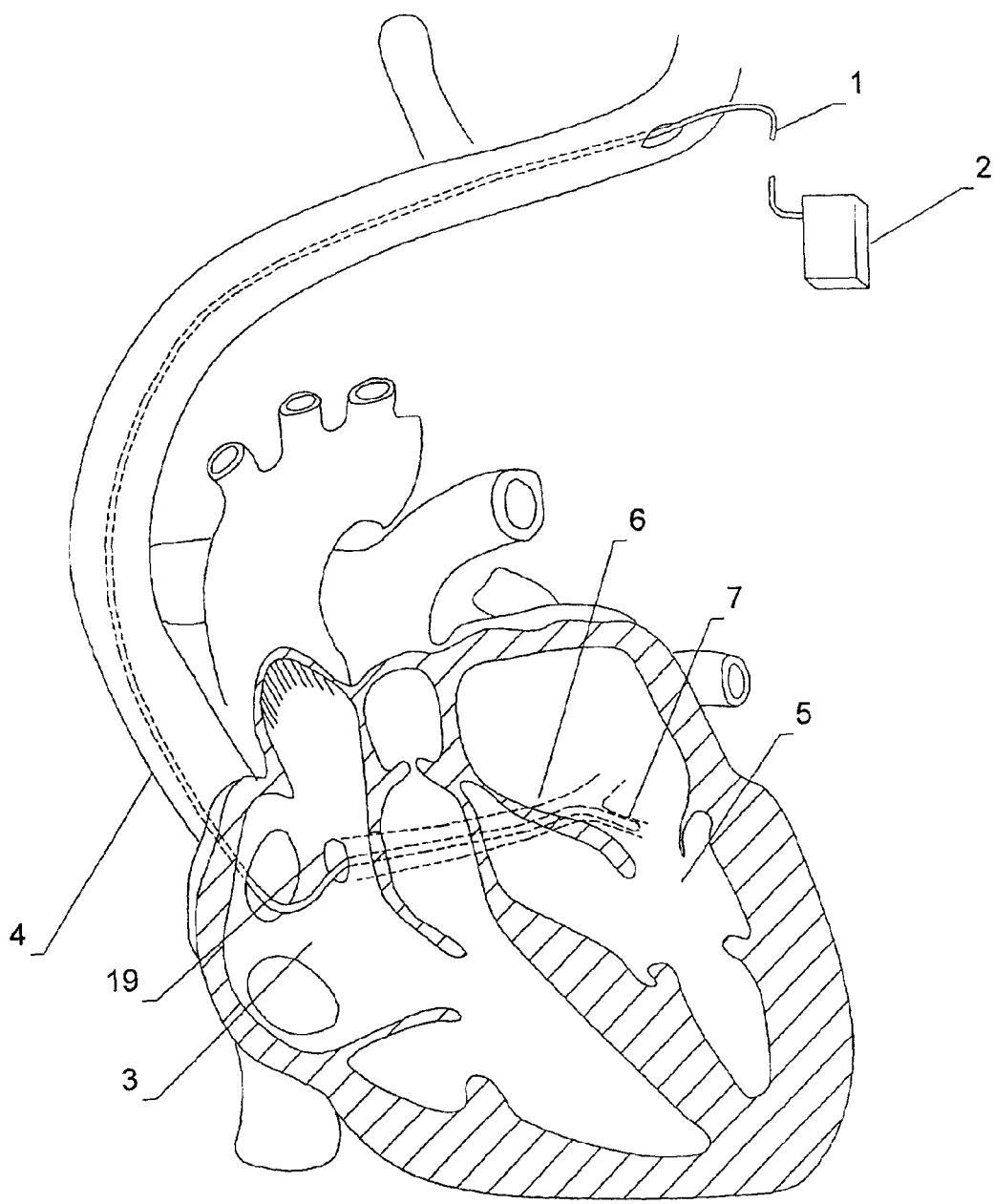
FIG. 1 is a view of the heart showing an apparatus according to the present invention implanted in the coronary sinus.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Various measures have been developed to characterize reduced cardiac function. One such measure is hemodynamic state, which can be loosely defined as the physics of blood flow in the circulation system. Estimating hemodynamic state includes measuring physical parameters of blood such as pressure and temperature. The measurements can be taken from various chambers within the heart, including the left and right ventricles. Hemodynamic measurements from the left ventricle are considered particularly useful.

Given that the hemodynamic state can be a useful and accurate indicator of heart performance, the hemodynamic state parameters can be beneficially utilized to adaptively change the timing and/or synchronization of a cardiac pacing or defibrillation system. Further, analyzing hemodynamic state can provide a pacing system with the ability to measure and adapt to heart activity over a long period of time in order to measure and improve the efficacy of the pacing therapy for the CHF patient.

The work done by the left ventricle results in heat being added to the blood pumped through the left ventricular myocardium. This blood is collected in coronary veins, passes through the great vein (i.e. the coronary sinus), and then moves into the right atrium through the coronary sinus ostium. Once the blood reaches the right atrium, it mixes with cooler peripheral blood and the workload information is lost. A system according to the present invention uses a temperature reading obtained from blood in a coronary vein, thereby determining blood temperature before the blood reaches the right atrium. Such a blood temperature reading can be used to calculate workload of the left ventricle.

Turning now to FIG. 1, a system according to the present invention is shown deployed within a heart. The system includes a lead system 1 that is designed for implantation in a coronary vein, preferably the great vein, for a pacing treatment such as cardiac resynchronization therapy (CRT). The lead system 1 has an elongated shape with dimensions suitable for intravenous implantation. A detector/energy delivery system 2 is coupled to the lead system 1. The detector/energy delivery system 2 measures electrical signals from the lead system 2.

The detector/energy delivery system 2 typically includes a power supply and programmable circuit (e.g. microprocessor) coupled to an analog to digital (A-D) converter. Various lead system devices, such as electrodes and thermal sensors, can interface to the A-D converter for sensing/data collection. Alternatively, analog conditioning (e.g. filtering) may be applied to sensor signals before interfacing with the A-D converter. The detector/energy delivery system 2 also utilizes an energy delivery system. The energy delivery system may include charge capacitors and signal conditioning circuitry known in the art. The energy system may interface to the programmable circuit through a D-A converter.

A system according to the present invention may also be adapted for monitoring purposes only, in which case the detector/energy delivery system 2 may not require an energy delivery system. Further, although the detector/energy delivery system 2 is typically implantable, it can be appreciated that a detector/energy delivery system 2 can be externally located, in whole or in part, in some applications, such as a temporary installation or in clinical testing.

The detector/energy delivery system 2 uses the measured signals from sensor devices to detect cardiac performance data such as rhythmic anomalies. If anomalies are detected, the detector/energy delivery system 2 can apply electrical impulses to the heart through the lead system 1 to restore and maintain normal heart rhythm.

The lead system 1 is implanted into the coronary sinus using various techniques. One such technique, as illustrated in FIG. 1, involves creating an opening in a percutaneous access vessel such as the left subclavian or left cephalic vein. The pacing lead is guided into the right atrium 3 of the heart via the superior vena cava 4. From the right atrium 3, the lead system 1 is sent into the coronary sinus ostium 19. The ostium 19 is the opening of the coronary sinus 6 into the right atrium 3. The lead system 1 is guided through the coronary sinus 6 to a coronary vein 7 of the left ventricle 5. A distal end of the lead system 1 is lodged into the coronary vein 7.

Figure 2:
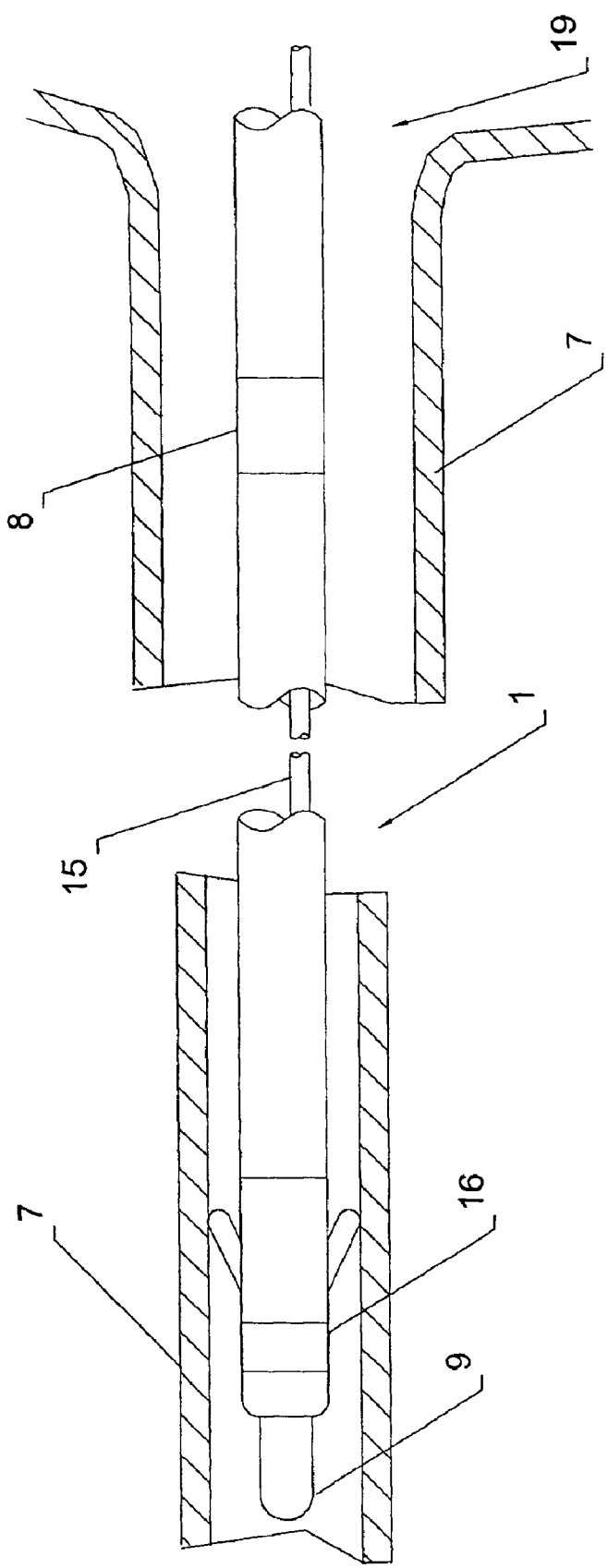
FIG. 2 is a view of a system according to the present invention implanted in a coronary vein.

FIG. 2 shows a distal end of the lead system 1 within the coronary vein 7. The lead system 1 includes at least one thermal sensor 9 at a distal tip. The thermal sensor 9 can include a thermistor exposed to the bloodstream. Other temperature transducers are known in the art and can be included in the thermal sensor 9. Such temperature transducers include thermocouples, infrared detectors, fiber optic detectors, and micro-electrical-mechanical systems (MEMS). MEMS technology uses semiconductor techniques to build microscopic mechanical devices in silicon or similar materials. The thermal sensor 9 is coupled to one or more conductors 15 disposed along the length of the lead system 1. In the configuration shown in FIG. 2, the thermal sensor 9 is integrated with the lead system 1.

An alternate thermal sensor arrangement is also shown in FIG. 2, where a thermal sensor 8 is mounted on the elongated body of the lead system 1 proximal to an electrode 16 mounted at a distal end of the lead system 1. In this location, the thermal sensor 8 can obtain an averaged blood temperature of all coronary veins emptying into the coronary sinus 7. The thermal sensor is best located distal to the coronary sinus ostium 19 when the lead system 1 is positioned in the coronary vein 7. In most cases, mounting the thermal sensor 8 about 5 cm to about 10 cm from the distal tip of the lead system 1 will provide a suitable location for measuring an averaged blood temperature in the coronary sinus.

Figure 3:
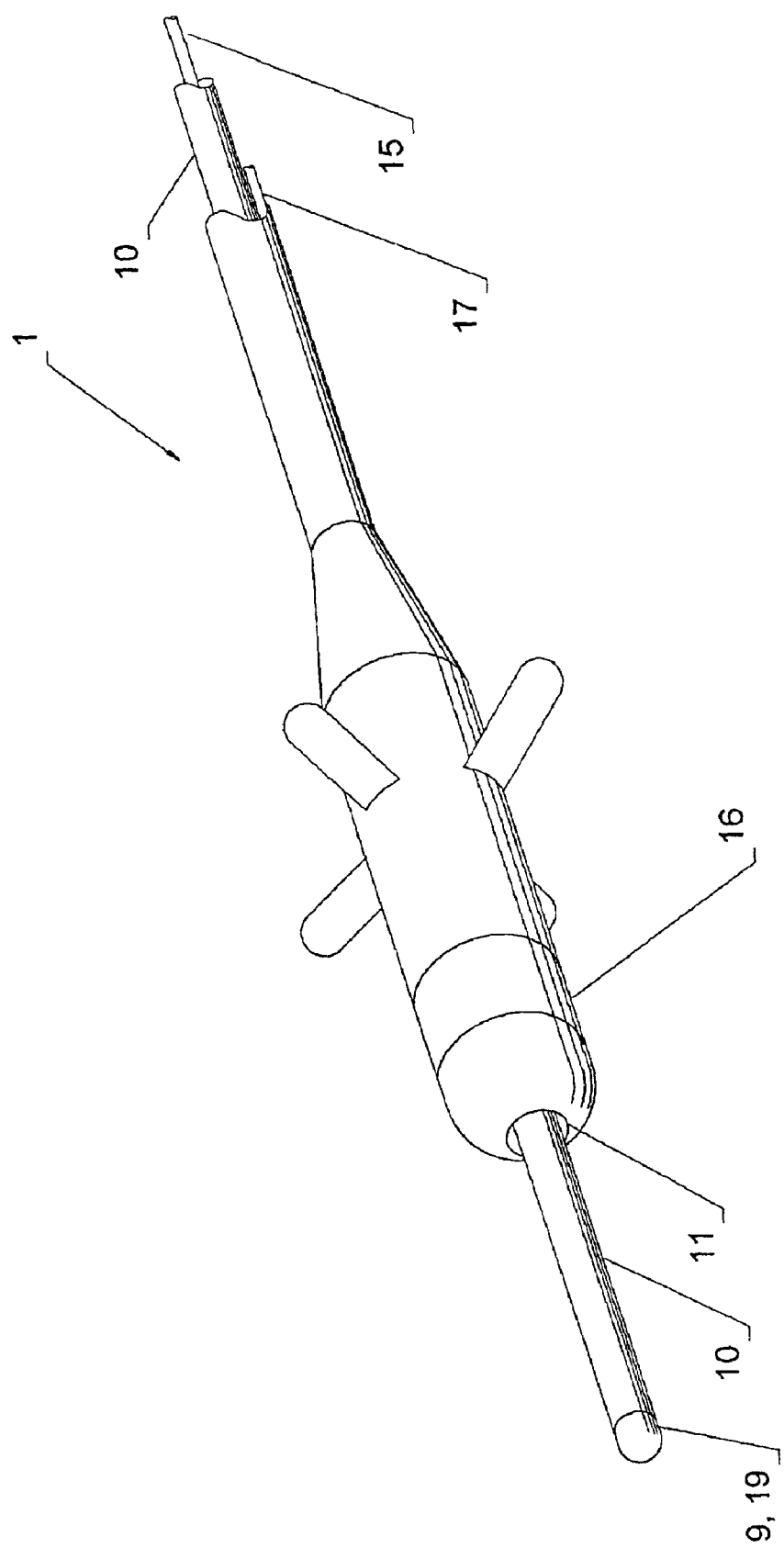
FIG. 3 is an external view of a distal end of an apparatus embodying features of the present invention.

FIG. 3 shows an alternate configuration of a thermal sensor 9. The thermal sensor 9 is mounted to a distal tip of a catheter 10. The catheter 10 is sized such that it can be movably disposed within an open lumen 11 of the lead system 1. The lead system 1 may already include an open lumen 11 for an over-the-wire installation technique. After lead system installation, the catheter 10 can be distally advanced through the lead system 1 until a distal tip of the catheter 10 extends past the distal tip of the lead system 1. This advantageously allows the orientation of the thermal sensor 9 to be adjusted during installation to account for effects caused by nearby anatomical features. After the catheter 10 has been positioned satisfactorily, it can be secured to the lead system 1 and coupled to the detector/energy delivery system 2 (shown in FIG. 1).

At least one electrode 16 is also disposed on a distal end of the lead system 1. The electrode 16 is utilized to read electrical signals from the heart and apply synchronized electrical impulses to the heart tissue to pace the heart. In one configuration, two or more electrodes 16 are utilized, with an electrode 16 used for reading electrical signals while one or more electrodes 16 are used for applying electrical impulses. The electrode 16 is coupled to at least one conductor 17, the conductor 17 running along the length of the lead system 1. The construction and use of pacing lead electrodes 16 is well known in the art.

In a system according to the present invention, the electrical impulses delivered to the electrode 16 can be adaptively adjusted by the detector/energy delivery system 2 based on temperature outputs from the thermal sensor 9. The thermal sensor 9 of a system according to the present invention can measure the temperature of the blood returning through the coronary sinus after having passed through myocardial tissue. As a byproduct of normal cardiac function, the heart generates heat. This heat is extracted by the perfusing blood. The blood exits through the coronary veins into the coronary sinus before passing into the right atrium and right ventricle. The blood is then pumped through the lungs where the excess heat is removed and passed out of the body with the exhaled air.

The difference in temperature between blood entering the left ventricle and blood in a coronary vein is related to left ventricular work, and the relationship is linear if corrected for the coronary sinus flow rate. The measured temperature can, in one application, be used to control the pacing rate in a rate-adaptive pacemaker. For example, a long-term (on the order of hours) average temperature can be stored in the detector/energy delivery system 2. The long-term average temperature is measured predominantly from a resting state. The detector/energy delivery system 2 can measure and continually update the long-term average based on sample readings from the thermal sensor 9.

The detector/energy delivery system 2 can use the difference between the current temperature and the long term average temperature to derive heart rate, such as by use of the following equation:

$$\text{Rate} = \text{Rate}_{Rest} + k \cdot (T_{Current} - T_{Avg}) \quad [1]$$

where, k is a programmed slope factor. The slope factor k can be expressed in units of beats/(min °C.).

The difference between the current temperature and a long-term average temperature could also be used as an activity indicator, since increased temperature with a relatively short rise time (on the order of seconds or minutes) would be indicative of increased activity. Indications of increased temperature can be combined with other indicators of activity, such as increased respiratory rate, to form a more accurate indicator of activity.

The long-term temperature, $T_{Avg}$, should be updated over time by the detector/energy delivery system 2 such that a running average temperature is maintained that reflects the patient's current metabolic state. Such temperature updates are ideally made when the patient is at rest. A system according to the present invention can advantageously utilize an implantable activity sensor to determine the metabolic demand of the patient, and thereby determine allowable times in which to update the patient's long-term temperature, $T_{Avg}$.

Various forms of activity sensors are known in the art. In one configuration, an accelerometer is coupled within the detector/energy delivery system 2. As the patient's activity level increases, the amplitude and the frequency of signals produced by the accelerometer correspondingly increase. A programmable circuit within the detector/energy delivery system 2 can interpret this signals to determine the current metabolic demand.

Another activity sensor adaptable for use with the present invention includes a minute ventilation sensor. A minute ventilation sensor is more sensitive to respiratory demands associated with exertion or difficult breathing in comparison to an accelerometer. An exemplary minute ventilation sensor uses the principle of impedance plethysmography, where the electrical impedance of lung tissue is monitored and changes in electrical impedance are interpreted as changes in the volume of air in the lungs. Higher impedance would result from more air and less blood in the lung following inhalation, where the lower impedance would result from less air and more blood in the lung, as a result of expiration. Each pulse in the resulting electrical impedance waveform would correspond to a breath.

A system according to the present invention can measure minute ventilation by emitting a low-voltage carrier signal from a distal end of the lead system 1. Since bodily tissue acts as a conductor, the emitted carrier signal can be picked up at a conductive surface of the detector/energy delivery system 2. Respiration, as well as other systolic activity, changes the impedance between the distal end of the lead system 1 and the detector/energy delivery system 2, thereby modulating the carrier signal. The detector/energy delivery system 2 can filter and process this signal to obtain an accurate measure of respiratory rate.

To determine whether the patient is at a state of rest, the detector/energy delivery system 2 can be programmed with parameters that are unique to a particular patient. For example, a respiration rate of 12–20 breaths per minute is considered a normal range for adults. A more representative respiration for the implant patient can be measured and stored in the detector/energy delivery system 2 prior to use. In a system that includes an accelerometer activity sensor, acceleration profiles for normal human activity are easy to obtain and/or measure. These profiles can be used for programming the detector/energy delivery system 2 to set thresholds of activity wherein the patient can be considered at rest.

In a system utilizing one or more activity sensors, an increase in coronary vein blood temperature without an associated increase in other activity indicators may be a sign that that work performed by the heart is increasing without an appropriate stimulus. This is indicative of reduced hemodynamic efficiency. A system according to the present invention can use indicators of reduced hemodynamic efficiency to adaptively adjust parameters of the CRT.

In some cases, it has been found that CRT can be adjusted to reduce myocardial work. A system according to the present invention can optimize programming of a device parameter (e.g., AV Delay) by changing the parameter and looking for decreases in temperature. In such an arrangement, the CRT can be adaptively optimized based on individual patient physiology and metabolism.

Other parameters of the hemodynamic state of a patient's heart can be measured with a system according to the present invention. These hemodynamic state parameters can be used to monitor patient health and to improve the efficacy of a pacing therapy. The useful work ($W_U$) performed by the left ventricle relates to the volume of blood moved through the ventricle, whereas the heat output from the left ventricle is related to total work ($W_T$). A useful measure of hemodynamic efficiency, E, can be calculated from the following equation:

$$E = W_U/W_T \quad [2]$$

The temperature sensor 9 of a system according to the present invention provides a measure of heat output at the left ventricle, $T_{CV}$. As blood enters the left ventricle from the aorta, it has a temperature $T_{AORTA}$. The total work, $W_T$, is related to the rise in temperature of blood, and can be estimated according to the following equation:

$$W_T = c(T_{CV} - T_{AORTA}) \quad [3]$$

where, c is a constant (heat capacity). Equation [3] assumes a constant blood flow rate. The assumption of a constant blood flow rate is reasonable if the temperature measurements are made when the patient is at a state of rest.

Figure 4:
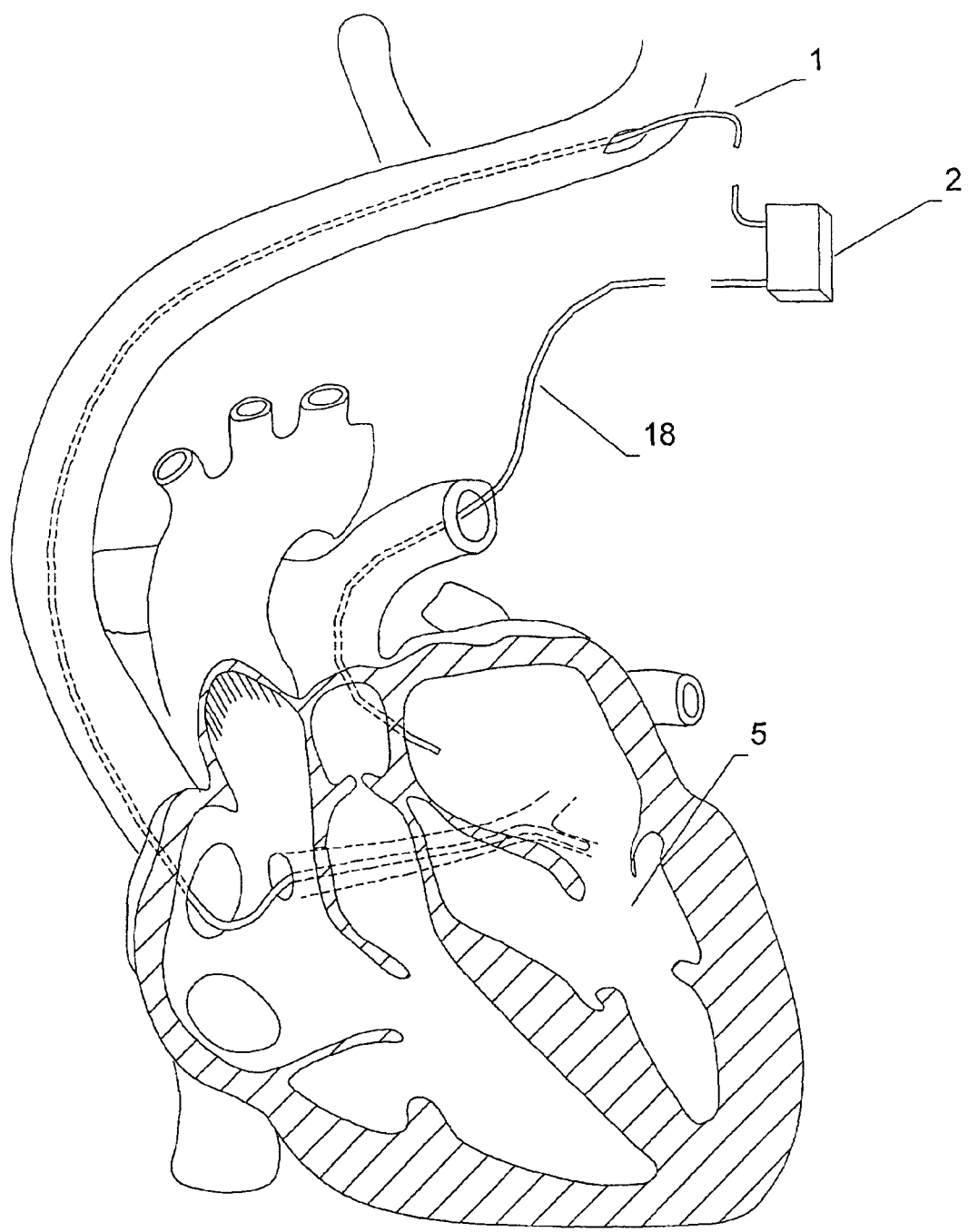
FIG. 4 is a view of the heart showing a system according to the present invention utilizing a ventricular thermal sensor.

To provide an accurate indicator of total work according to equation [3], the temperature of blood entering the left ventricle, $T_{AORTA}$, is a useful measurement. In one configuration of a system according to the present invention, a temperature reading is taken from a sensor measuring blood temperature from the aorta or left ventricle as shown in FIG. 4. The temperature sensor 18 is connected to the detector/energy delivery system 2 that can utilize a programmable circuit to calculate total work based on $T_{CV} - T_{AORTA}$.

If it is assumed $T_{AORTA}$ is constant at rest, a change in total work is found by the equation:

$$W_T = W_{REST} + cT_{CV} \quad [4]$$

where, $W_{REST}$ is a constant. An increase in $W_T$ that is not accompanied by other indications of increased activity will result in a lowering of efficiency, E. Upon detecting a lower efficiency, the detector/energy delivery system can apply small changes to the synchronization of electrical pulses in order to decrease $T_{CV}$, and thereby increase hemodynamic efficiency.

It is also useful to look at the power generated by cardiac activity. The average cardiac power, $P_{cardiac}$, is the energy being utilized by the heart that is converted into heat. $P_{cardiac}$ is work per volume times the flow rate in the coronary sinus ($FLOW_{CV}$). This can be computed by:

$$P_{cardiac} = c(T_{CV} - T_{AORTA}) \cdot FLOW_{CV} \quad [5]$$

Since all of the blood perfusing the left ventricle passes through the coronary sinus, a measure of flow in this body accurately reflects the total blood flow through myocardial tissue. This flow is measured in ml/min and thus the final power, $P_{cardiac}$, is measured in units of joules/(ml·deg)·deg·(ml/min)=joules/min. Any change in cardiac function that maintains or increases cardiac output while reducing cardiac power can be considered to improve cardiac efficiency. These measurements may also be expressed in terms of joules/beat. This would correspond to the work done in a single heartbeat.

Cardiac output can be measured by inferring the stroke volume from left or right ventricular impedance and multiplying by the heart rate. Exemplary methods of using electrical leads to determine ventricular impedance are disclosed in commonly-owned U.S. Pat. Nos. 6,278,894, 4,674,518, 4,686,987, 5,036,849, and 5,190,035, which are hereby incorporated herein by reference.

Cardiac output can also be assumed to be proportional to the blood flow through the coronary vein ($FLOW_{CV}$). This second approach, though less accurate, is attractive because cardiac efficiency, E, can then be expressed as:

$$P_{external} = a \cdot FLOW_{CV} \quad [6]$$

$$E = P_{external}/P_{cardiac} = a/[b \cdot (T_{CV} - T_{AORTA})] \quad [7]$$

$$E = k/(T_{CV} - T_{AORTA}) \quad [8]$$

Thus, as seen in equation [8], efficiency is inversely proportional to the temperature difference across the myocardium. An improvement in efficiency will thereby be reflected in a decrease in the temperature difference. If the actual cardiac output is measured by another technique (such as ventricular impedance), the effect of the temperature difference will be moderated by the relative distribution of blood flow to the heart. However, myocardial oxygen consumption is usually well correlated with overall work load so that the percentage of total blood that perfuses the myocardium remains relatively constant.

Since efficiency is inversely proportion to $T_{CV} - T_{AORTA}$ (equation [8] above), it is important to determine the temperature of blood in the aorta or left ventricle. However, if the patient is at rest, it can be assumed that the aortic temperature remains approximately constant and that any reduction in $T_{CV}$ is due to an improvement in efficiency. Thus, one could optimize any therapy parameter with respect to efficiency by varying the parameter and looking for the minimum coronary sinus temperature.

A more accurate measure of external cardiac work involves the computation of stroke work, which is the area under a pressure-volume (PV) loop. A PV loop is generated on a Cartesian graph by plotting the ventricular pressure on the graph's ordinate and ventricular volume on the graph's abscissa. To accurately determine stroke work, a configuration of the present invention may integrate a pressure sensor 19 with a temperature sensor 9 in the lead system 1 (best seen in FIG. 3). A MEMS sensor, for example, can integrate both pressure and temperature sensors into a single assembly deployable at the distal end of the lead system 1. The pressure sensor 19 can obtain a coronary vein reading that is proportional to the actual left ventricular pressure. By way of example, an implantable lead system utilizing a distal pressure sensor is disclosed in commonly-owned U.S. patent application entitled "Method And Apparatus for Measuring Left Ventricular Pressure," filed under Attorney Docket No. 1275.47US01.

The ventricular pressure can be measured as discussed in 1275.47US01 and the volume measured by ventricular impedance. A stroke work (external work) measurement is obtained by the detector/energy delivery system 2 in this manner for each heartbeat. The total cardiac work can be obtained using equation [5] with the flow measured over each heartbeat. This provides a cardiac work measurement for each heartbeat. The efficiency for each beat would then be defined as external cardiac work/total cardiac work, or $W_u/W_t$ as shown in equation [2].

Using measurements of left ventricle flow and pressure allows a system according to the present invention to accurately determine cardiac efficiency of the heart. By utilizing flow and blood temperature measurements, a detector/energy delivery system can determine and store hemodynamic state data. Besides allowing the active adjustment of pacing therapy, this hemodynamic state data can be accessed by a physician to accurately characterize a patient's cardiac condition. Such characterizations allow the physician to provide more effective therapy for heart disease patients.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A body implantable system, comprising:
    a lead system comprising an elongated body, an open lumen, and at least one electrode at a distal end of the lead system;
    a sensing catheter movably disposed within the open lumen of the lead system, a distal tip of the sensing catheter extending beyond a distal tip of the lead system, the sensing catheter comprising at least one thermal sensor at a distal end of the sensing catheter; and
    a detector/energy delivery system coupled to the lead system, the detector/energy delivery system sensing ventricular rhythms from the at least one electrode and sensing blood temperature from the at least one thermal sensor, the detector/energy delivery system delivering an electrical signal to the at least one electrode.

2. The system of claim 1, wherein the thermal sensor comprises a thermistor.

3. The system of claim 1, wherein the thermal sensor comprises a MEMS temperature sensor.

4. The system of claim 1, wherein the thermal sensor comprises a thermocouple.

5. The system of claim 1, wherein the thermal sensor comprises a fiber optic temperature probe.

6. The system of claim 1, wherein the detector/energy delivery system modifies the delivery of electrical signals based on the sensed blood temperature.

7. The system of claim 1, further comprising a flow sensor for sensing a cardiac output, and wherein the detector/energy delivery system further senses a left ventricular flow rate from the flow sensor.

8. The system of claim 7, wherein the flow sensor comprises a ventricular impedance sensor.

9. The system of claim 7, wherein the detector/energy delivery system determines a hemodynamic efficiency of the heart using the sensed left ventricular flow rate and the sensed blood temperature.

10. The system of claim 7, wherein the detector/energy delivery system modifies the delivery of electrical signals based on the sensed left ventricular flow rate and the sensed blood temperature.

11. The system of claim 1, further comprising a ventricular thermal sensor for sensing a blood temperature entering the left ventricle, the ventricular thermal sensor coupled to the detector/energy delivery system, and wherein the detector/energy delivery system further senses a temperature difference between the ventricular thermal sensor and the at least one thermal sensor at a distal end of the sensing catheter.

12. The system of claim 11, wherein the detector/energy delivery system determines a hemodynamic efficiency of the heart using the sensed temperature difference.

13. The system of claim 11, wherein the detector/energy delivery system modifies the delivery of electrical signals based on the sensed temperature difference.

14. The system of claim 1, further comprising an activity sensor coupled to the detector/energy delivery system.

15. The system of claim 14, wherein the activity sensor comprises an accelerometer.

16. The system of claim 14, wherein the activity sensor comprises a minute ventilation sensor.

17. The system of claim 14, wherein the detector/energy delivery system updates a long term average blood temperature measurement from the at least one thermal sensor, the long term average blood temperature updated at a state of rest as sensed by the activity sensor.

* * * * *